United States Patent
Anderson et al.

(10) Patent No.: US 9,370,449 B2
(45) Date of Patent: Jun. 21, 2016

(54) PHOTOTHERAPY DRESSING FOR TREATING PSORIASIS

(71) Applicant: Luma Therapeutics, Inc., Millbrae, CA (US)

(72) Inventors: Evan Anderson, Redwood City, CA (US); Christopher Pell, San Francisco, CA (US); Stephen Dugan, San Francisco, CA (US); Adam Martos, Santa Cruz, CA (US)

(73) Assignee: Luma Therapeutics, Inc., Millbrae, CA (US)

( * ) Notice: Subject to any disclaimer, the term of this patent is extended or adjusted under 35 U.S.C. 154(b) by 0 days.

(21) Appl. No.: 14/632,161

(22) Filed: Feb. 26, 2015

(65) Prior Publication Data

US 2015/0238774 A1    Aug. 27, 2015

Related U.S. Application Data

(60) Provisional application No. 61/944,755, filed on Feb. 26, 2014, provisional application No. 62/049,366, filed on Sep. 12, 2014.

(51) Int. Cl.
*A61F 13/00* (2006.01)
*A61K 35/04* (2006.01)
(Continued)

(52) U.S. Cl.
CPC ....... *A61F 13/00063* (2013.01); *A61F 13/0213* (2013.01); *A61N 5/0616* (2013.01);
(Continued)

(58) Field of Classification Search
CPC ..... A61K 9/0014; A61K 31/12; A61K 35/04; A61L 26/0066; A61L 26/008; A61L 26/0095; A61N 5/0616; A61N 5/062; A61N 2005/0645; A61N 2005/0661; Y10S 514/863
USPC .................................. 606/88, 89; 604/20
See application file for complete search history.

(56) References Cited

U.S. PATENT DOCUMENTS 4,102,995 A * 7/1978 Hebborn ................... 424/725.1
4,309,007 A   1/1982 Logsdon
(Continued)

FOREIGN PATENT DOCUMENTS

EP    1858503 B1    9/2013
WO   2009066294 A1   5/2009

OTHER PUBLICATIONS

MG217 (http://www.mg217.com/products/medicated-coal-tar-gel/) accessed on Aug. 18, 2015 and backdated to Oct. 24, 2013 using https://web.archive.org/web/20131024170120/http://www.mg217.com/productsmg217/.*

(Continued)

*Primary Examiner* — Lynsey Crandall
*Assistant Examiner* — Nathan J Jenness
(74) *Attorney, Agent, or Firm* — Shay Glenn LLP

(57) ABSTRACT

Methods and apparatuses for phototherapy to treat skin disorders. In particular, described herein are phototherapy dressings for use with phototherapy UV light applicators (sources) to treat skin disorders such as psoriasis. The dressings described herein may include a support body onto which a medicament formed of a hydrogel and coal tar and/or coal tar extract is held. The dressing may be configured so that at least half (50%) of the UV light within a therapeutic range of wavelengths is through the dressing including the medicament to the patient's skin. The dressings may be adapted for use in conjunction with a phototherapy UV light sources.

29 Claims, 8 Drawing Sheets

(51) Int. Cl.
    *A61L 26/00* (2006.01)
    *A61F 13/02* (2006.01)
    *A61N 5/06* (2006.01)

(52) U.S. Cl.
    CPC ............ *A61K 35/04* (2013.01); *A61L 26/0066* (2013.01); *A61N 2005/0645* (2013.01); *A61N 2005/0661* (2013.01)

(56) References Cited

U.S. PATENT DOCUMENTS

| | | | |
|---|---|---|---|
| 4,341,783 A * | 7/1982 | Scheindlin | 514/263.34 |
| 4,440,777 A | 4/1984 | Zupan | |
| 5,300,097 A | 4/1994 | Lerner et al. | |
| 5,393,798 A | 2/1995 | Weber | |
| 5,474,528 A | 12/1995 | Meserol | |
| 5,501,849 A | 3/1996 | Lee | |
| 5,616,140 A | 4/1997 | Prescott | |
| 5,658,956 A | 8/1997 | Martin et al. | |
| 5,695,778 A | 12/1997 | List | |
| 5,827,529 A | 10/1998 | Ono et al. | |
| 5,836,999 A | 11/1998 | Eckhouse et al. | |
| 5,879,292 A | 3/1999 | Sternberg et al. | |
| 5,958,420 A | 9/1999 | Jenson | |
| 5,989,245 A * | 11/1999 | Prescott | 606/14 |
| 6,045,575 A | 4/2000 | Rosen et al. | |
| 6,050,990 A * | 4/2000 | Tankovich et al. | 606/9 |
| 6,096,066 A * | 8/2000 | Chen et al. | 607/88 |
| 6,231,593 B1 | 5/2001 | Meserol | |
| 6,238,691 B1 * | 5/2001 | Huang | 424/443 |
| 6,290,713 B1 | 9/2001 | Russell | |
| 6,436,127 B1 | 8/2002 | Anderson et al. | |
| 6,443,978 B1 | 9/2002 | Zharov | |
| 6,663,659 B2 | 12/2003 | McDaniel | |
| 6,730,113 B2 | 5/2004 | Eckhardt et al. | |
| 6,955,684 B2 | 10/2005 | Savage et al. | |
| 6,984,228 B2 | 1/2006 | Anderson et al. | |
| 6,986,782 B2 | 1/2006 | Chen et al. | |
| 7,018,647 B1 | 3/2006 | Yamasaki et al. | |
| 7,052,167 B2 | 5/2006 | Vanderschuit | |
| 7,177,695 B2 | 2/2007 | Moran | |
| 7,198,624 B2 | 4/2007 | Muzzi et al. | |
| 7,267,673 B2 | 9/2007 | Pilcher et al. | |
| 7,276,059 B2 | 10/2007 | Irwin | |
| 7,304,201 B2 | 12/2007 | Holloway et al. | |
| 7,723,910 B2 | 5/2010 | Lundahl et al. | |
| 7,740,875 B2 | 6/2010 | Dechow | |
| 7,820,177 B2 | 10/2010 | Kruse et al. | |
| 7,886,749 B2 | 2/2011 | Irwin | |
| 7,887,842 B2 | 2/2011 | Koo et al. | |
| 7,918,229 B2 | 4/2011 | Cumbie et al. | |
| 7,989,165 B2 | 8/2011 | Benson | |
| 8,067,376 B2 | 11/2011 | Lee et al. | |
| 8,096,982 B2 | 1/2012 | Nemati | |
| 8,142,486 B2 | 3/2012 | Quisenberry et al. | |
| 8,253,787 B2 | 8/2012 | Yamamoto | |
| 8,303,982 B2 | 11/2012 | Smith et al. | |
| 8,372,128 B2 | 2/2013 | Reuben | |
| 8,376,232 B2 | 2/2013 | Eckstein | |
| 8,399,731 B2 | 3/2013 | Meyer | |
| 8,449,587 B2 | 5/2013 | Cornil | |
| 8,449,913 B2 | 5/2013 | Koo et al. | |
| 8,486,056 B2 | 7/2013 | Irwin | |
| 8,512,718 B2 | 8/2013 | Eini et al. | |
| 8,563,799 B2 | 10/2013 | Kamakura et al. | |
| 8,620,451 B2 | 12/2013 | Kennedy | |
| 8,668,727 B2 | 3/2014 | Natale et al. | |
| 8,760,295 B2 | 6/2014 | Forster | |
| 8,801,254 B2 | 8/2014 | McNeill et al. | |
| 2004/0186082 A1 * | 9/2004 | Hartman | 514/167 |
| 2006/0085053 A1 | 4/2006 | Anderson et al. | |
| 2006/0173514 A1 * | 8/2006 | Biel et al. | 607/88 |
| 2007/0207222 A1 | 9/2007 | Yu et al. | |
| 2007/0233208 A1 * | 10/2007 | Kurtz et al. | 607/88 |
| 2008/0020383 A1 * | 1/2008 | Koshy et al. | 435/6 |
| 2008/0206161 A1 * | 8/2008 | Tamarkin et al. | 424/45 |
| 2009/0312751 A1 | 12/2009 | Ockenfels | |
| 2010/0161009 A1 * | 6/2010 | Forster | 607/88 |
| 2010/0286673 A1 * | 11/2010 | Altshuler et al. | 606/9 |
| 2011/0002918 A1 * | 1/2011 | Levatter | 424/133.1 |
| 2011/0264174 A1 | 10/2011 | McNeill et al. | |
| 2011/0287113 A1 | 11/2011 | Davis et al. | |
| 2012/0040971 A1 | 2/2012 | Glick | |
| 2012/0101557 A1 | 4/2012 | Cacciola et al. | |
| 2012/0109042 A1 | 5/2012 | Koo et al. | |
| 2012/0289885 A1 | 11/2012 | Cottrell et al. | |
| 2012/0320340 A1 | 12/2012 | Coleman | |
| 2013/0115268 A1 | 5/2013 | Koo et al. | |
| 2013/0116616 A1 | 5/2013 | Buchholz et al. | |
| 2013/0144364 A1 | 6/2013 | Cacciola et al. | |
| 2013/0178919 A1 | 7/2013 | McNeill | |
| 2013/0274834 A1 | 10/2013 | Barolet et al. | |
| 2014/0074010 A1 | 3/2014 | Veres et al. | |

OTHER PUBLICATIONS

International Search Report and Written Opinion mailed Jun. 5, 2015 from International Application No. PCT/US2015/017664 filed Feb. 26, 2015.
Crow, Photosensitivity Due to Pitch, 1961, pp. 220-232.
Lebwohl et al., Effects of Topical Preparations on the Erythemogenicity of UVB: Implications for Psoriasis Phototherapy, Journal of the American Academy of Dermatology, Mar. 1995, pp. 469-471.
Berne et al., "The UV Erythema Action Spectra of Three Coal Tar Preparations", Clinical and Experimental Dermatology, 1987, 12, pp. 400-402.
Tanenbaum, et al., "Tar Phototoxicity and Phototherapy for Psoriasis", Arch. Dermatol., vol. 111, Apr. 1975, pp. 467-470.
Merriam-Webster Dictionary, "Suspension", accessed at: http://www.merriam-webster.com/dictionary/suspension, 2015, 4 pgs.

* cited by examiner

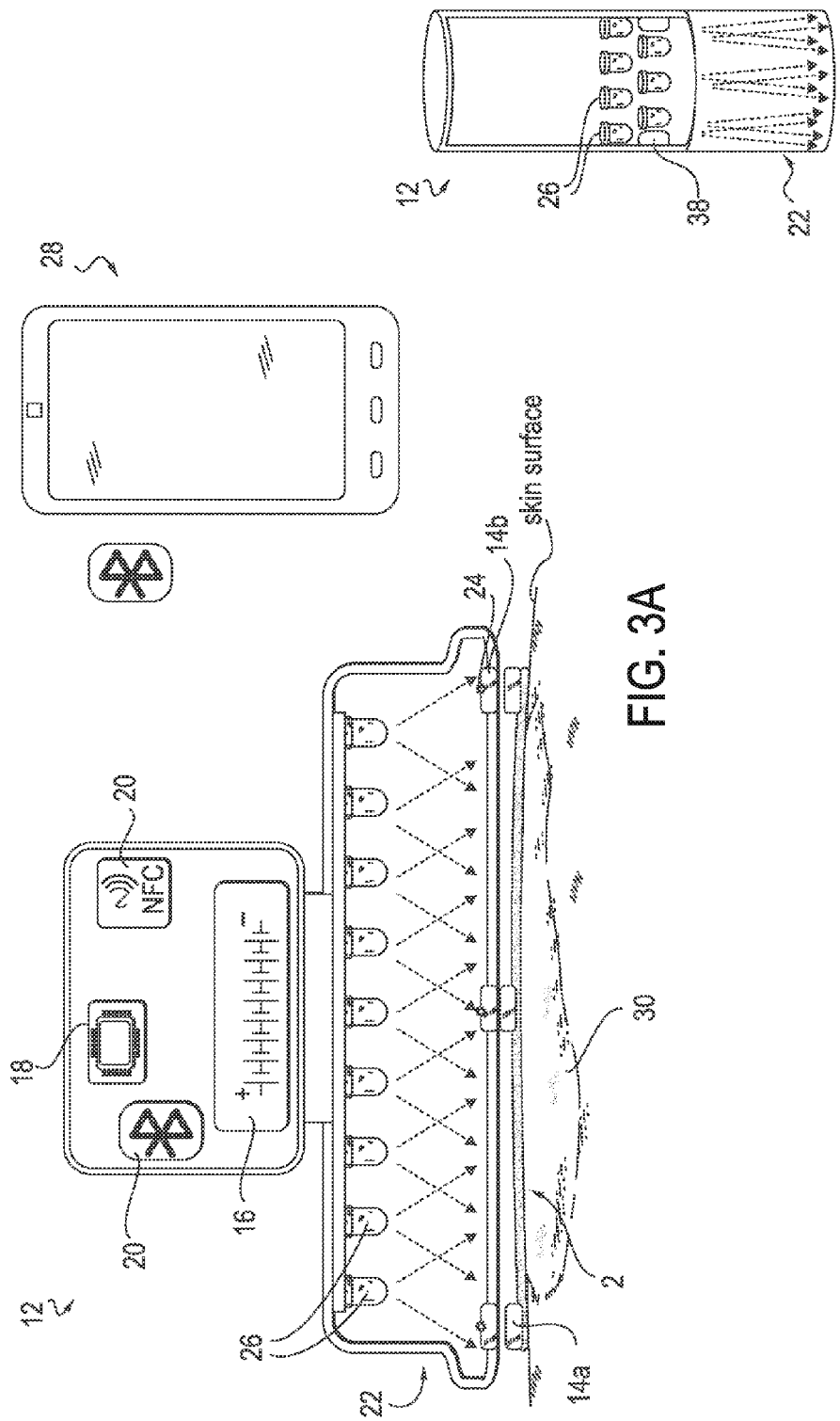

Determine dose based on:

- Type of disease
- Skin type
- Patient feedback on sensitivity of a lesion or group of lesions
- Previous dose history
- Amount absorbed by dressing if dressing is present
- Edge detection for recognition and guidance of light
- Amount of induration, scale or redness
- Location of lesion
- Thickness of epidermis

FIG. 6

PHOTOTHERAPY DRESSING FOR TREATING PSORIASIS

CROSS-REFERENCE TO RELATED APPLICATIONS

This application claims priority to U.S. provisional patent application Ser. No. 61/944,755, titled "Safe Therapeutic Light System", filed on Feb. 26, 2014; and U.S. provisional patent application Ser. No. 62/049,366, titled "Therapeutic Light System", filed Sep. 12, 2014, both of which are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are phototherapy methods and apparatuses, and specifically phototherapy methods, dressings, and UV light applicators for treating disorders, including phototherapy methods, dressings and applicators for treating psoriasis that are safe and easy to use by a patient at home.

BACKGROUND

Light, when delivered to the body, has been shown to elicit a wide range of therapeutic effects. Specifically, light can be used as a therapeutic agent for various disorders. Light, in the Ultraviolet (UV) spectrum, may be used as a treatment for skin disorders such as psoriasis, vitiligo, dermatitis, asteatotic, purigo, pruritis, etc. Light therapy is often delivered in a doctor's office or at home in chambers that deliver light to the entire body surface or with smaller light sources for delivery of light to focused areas of the body. Typically, a trained professional is required to deliver the light to ensure that the patient receives the correct dose of light and that sensitive areas, such as the eyes, are not exposed to the light.

In a light chamber, the amount of light delivered is based on the amount of time the patient is exposed to light. The light is delivered to the entire body even though the region that requires treatment often composes a fraction of the overall surface area of the body. When receiving this modality of light therapy, the patient must wear protective eyewear to prevent exposure of light to the eyes. If the patient is exposed to more light than intended, cellular damage and/or burns may occur over a large portion of the body, leading to significant discomfort and even medical treatment.

Using a focused light solves the issue of light exposure to areas that do not need therapy because the user directs the light to the area where the therapy is needed. When therapy is delivered at home and the user controls where the light is being delivered, there is increased risk of overexposure of one area of the body and underexposure of another area. In addition, the light can be inadvertently directed towards sensitive areas such as the eyes or genitals.

Further, there is evidence to show that light therapy treatment for skin disorders has been limited by patient's unwillingness to receive treatment in doctor's offices and lack of adherence to home light therapy systems. Adherence to therapy at home may be improved by increasing patient engagement and improving device ease of use.

Light therapy may also be combined with topical treatments. For example, coal tar is used as a therapeutic in conjunction with (though typically not at the same time) as phototherapy. For example, phototherapy with UVB has been used with coal tar (the Goeckerman regimen) as well as with anthralin. The Goeckerman regimen uses daily treatments for up to 4 weeks. The coal tar or anthralin is applied once or twice each day and then washed off before the procedure. Studies indicate that a low-dose (e.g., 1%) coal tar preparation is as effective as a high-dose (6%) preparation. Such regimens are unpleasant, but are still useful for some patients with severe psoriasis, because they can achieve long-term remission (up to 6-12 months). Treatments involving both UVB and coal tar or other topical drugs typically involve the separate application of the UVB and coal tar, in part because it coal tar is messy, odiferous and blocks or absorbs much of the delivered UV light. For this reason, coal tar is often applied after administration of the UVB. Unfortunately, bifurcating treatment in this way complicates the treatment, and may further limit the effectiveness. In addition, the use of a topical agent such as coal tar may be messy and unpleasant, at least in part because of the odor associated with the agent and the use of oil-based agents (e.g., petroleum) solubilizing the coal tar (or coal tar extract).

Thus, there is a need for apparatuses and methods for phototherapy, particularly for the treatment of skin disorders such as psoriasis, that are easy to use in even a home environment, and otherwise permit the application of therapeutic light to one or more specific areas of a patient's skin. The apparatuses and methods described herein may address these concerns.

SUMMARY

In general, described herein are methods and apparatuses (including devices and systems) that may be used to deliver phototherapy. In particular, described herein are phototherapy dressings, phototherapy UV light applicators (sources), and methods of using them to treat skin disorders such as psoriasis. The dressings described herein are generally adapted for use in conjunction with the phototherapy UV light sources; the dressing may be adapted to include one or more connectors (mechanical, magnetic/electromagnetic, etc.) for connecting with a UV light source. The UV light source may also or alternatively have a connector for connecting to the dressing, which may be complimentary to a corresponding connector or connector region on the dressing. The connector(s) may be oriented and/or configured so that the connection is oriented. In addition, the phototherapy dressings and phototherapy UV light sources described herein may also be configured to exchange information. For example, the dressing may include a unique identifier that can be read by the phototherapy UV light source and/or by a user device such as a hand-held computing device (e.g., smartphone, pad, etc.), which may also communicate with the UV light source. The unique identifier may include information specifically identifying the dressing (e.g., a model, make, batch, lot number, etc.) and this information may be associated with use information (e.g., number of phototherapy doses applied through the dressing, location of the dressing on the patient's skin, expiration date of the phototherapy dressing, etc.).

In general, the phototherapy dressings described herein include a medicament that is held against the patient's skin when the dressing is worn by the patient. The medicament may be a semisolid substance having a viscosity greater than water including and a drug or agent suspended in the semisolid substance. In particular, the semisolid substance may be a hydrogel and the drug or agent may be coal tar, e.g., coal tar or coal tar extract between about 0.1% and 5.0% in the hydrogel. Although these phototherapy dressings (which may be referred to herein as simply "dressings" or UV light dressings) may be particularly well suited for use with the phototherapy UV light applicators described herein, they may also or alternatively be used by themselves (e.g., to deliver the medicament) or with another device (e.g., thermal applicator devices, RF applicator devices, etc.).

In general, the dressings described herein are configured specifically so that they block only a fraction of UV light within a therapeutic range (e.g., 295 to 320 nm, or any subregion within this range), allowing UV light to be applied through the dressing onto the skin, while simultaneously applying the drug or agent (e.g., coal tar or coal tar extract) to the skin in a dressing that has a low moisture vapor transmission. Thus, the dressing may be configured so that the medicament (e.g., hydrogel and coal tar/coal tar extract) and the dressing (e.g., the region of the body of the dressing covering the medicament) permit more than a predetermined percentage of the UV light in the target frequency range to pass through the dressing and onto the skin beneath the dressing. The predetermined percentage of UV light may refer to any appropriate predetermined percentage, which may be selected based on the dosage and treatment time. For example, the predetermined percentage may be greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95%, etc. This may be expressed conversely, so that the dressing (or at least a treatment region of the dressing, e.g., forming an island region within the middle portion of the dressing) occludes less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, etc.

The dressing may be configured to pass UV light through the dressing for delivery to the subject's skin based on the material selected, such as the material forming the support body of the dressing as well as the material forming the medicament, as well as the dimensions (and particularly the thickness, e.g., in a direction normal to the skin when worn) and surface interfaces (e.g., textures) of these material. For example, the material forming the portion of the support body over the medicament may be a polymeric material with a relatively high transmission of UV light in the therapeutic frequency range desired. For example, relatively thin layers of polyurethane materials or polyester material, e.g., between about 0.001 to 0.005 inches thick. The medicament may generally include a high-water content semisolid material (such as a hydrogel) mixed with between about 0.1 and 5% coal tar and/or coal tar extract. The hydrogel may have a water content of between about 90 and about 99.5% water. The medicament may be coated or layered onto the support body and may also be relatively thin (e.g., having a thickness of between about 0.005 and about 0.1 inches (e.g., between about 0.01 inches to about 0.08 inches thick, e.g., between about 0.02 and about 0.05 inches thick, etc.). Surprisingly, the Applicants have found that that coal tar and coal tar extract do not require the use of an oil-based (e.g., petroleum) medium to suspend the material, but that a hydrogel will work, permitting UV transmission. In contrast, oil-based materials may occlude most of the UV light (e.g. greater than 90% even in very thin layers). Any appropriate hydrogel may be used, for example, hydrogels that are hydrophilic and primarily composed of water (e.g., deionized water, aloe vera gel, glycerine, sorbitol, carbomer 940, triethanolamine, allantoin, disodium EDTA, methylparaben, and imidazolidinyl urea), or the like. In one example, this hydrogel may be mixed with 2% coal tar (or 5% coal tar extract), and applied as a layer approximately 0.03 inches thick to a support body formed of polyurethane that is approximately 0.002 inches thick with a roughened surface to help adhere the medicament (hydrogel and coal tar/coal tar extract); this configuration will permit greater than half (50%) of the UV light at wavelengths between 300 and 320 to pass through the entire dressing. In some variations, coal tar extract (e.g., "Neutar") is purified, and may be used at a higher percent than coal tar relative to the occlusion of comparable levels of UV light. In addition to enhancing the UV transparency of the dressing, mixing the coal tar with a hydrogel (that may be substantially free of alcohol and/or oils typically used to dilute coal tar or coal tar extract) for topical use in a dressing may also significantly increases the efficacy of the tar. In particular, the dressings described herein may provide a moisture barrier that may both reduce the unpleasant odors of the coal tar/coal tar extract, and may improve efficacy.

In general a phototherapy dressing may include: a support body; a medicament in communication with the support body, the medicament including a semisolid substance having a viscosity greater than water including between about 0.1% and 5.0% coal tar or car tar extract; and an attachment for a phototherapy UV light source on the support body, wherein the attachment is configured to secure the phototherapy UV light source over the phototherapy dressing; wherein more than half of UV light emitted by the phototherapy UV light source at wavelengths between 300 and 320 nm passes through the phototherapy dressing, including the through the medicament.

For example, described herein are phototherapy dressings for skin disorders such as psoriasis. A phototherapy dressing may include: a support body having an island region; a medicament in communication with the island region, the medicament including a hydrogel including between about 0.1% and 5% coal tar or coal tar extract; wherein the medicament and island region together occlude less than 50% of UV light at wavelengths between 300 and 320 nm from passing through the phototherapy dressing; and a magnetic attachment for a phototherapy UV light source on the support body, the magnetic attachment configured to secure the phototherapy UV light source over the island region of the phototherapy dressing.

Any of the phototherapy dressings described herein may be phototherapy dressings for treating psoriasis and may include: a support body; a medicament in communication with the support body, the medicament including a hydrogel including between about 0.1% and 5% coal tar or coal tar extract; wherein the medicament and support body together occlude less than 50% of UV light at wavelengths between 300 and 320 nm from passing through the phototherapy dressing; an adhesive on the phototherapy dressing; and a magnetic attachment for a phototherapy UV light source on the support body, the magnetic attachment configured to secure the phototherapy UV light source to the phototherapy dressing.

As mentioned, the semisolid substance of the medicament may be a hydrogel. Any appropriate hydrogel may be used, particularly those that are substantially alcohol and oil (e.g., petroleum) free, e.g., having less than 0.1%, less than 0.05%, less than 0.01%, less than 0.005%, less than 0.001% of alcohol and/or oil, etc.). The semisolid (e.g., hydrogel) material may have a high water content (e.g., >90%, greater than 91%, greater than 92%, greater than 93%, greater than 94%, greater than 95%, greater than 96%, greater than 97%, greater than 98%, greater than 99%, 99.5% or more, etc. of water), and may include the coal tar (e.g., between about 0.01% and 10%, 0.01% and 7%, 0.1% and 8%, 0.1% and 7%, 0.1% and 6%, 0.1% and 5%, 0.1% and 4%, 0.1% and 3%, 0.1% and 2%, 0.1% and 1%, or any sub-region thereof) or coal tar extract (e.g., between about 0.01% and 10%, 0.01% and 7%, 0.1% and 8%, 0.1% and 7%, 0.1% and 6%, 0.1% and 5%, 0.1% and 4%, 0.1% and 3%, 0.1% and 2%, 0.1% and 1%, or any sub-region thereof).

Any of the phototherapy dressings described herein may include an adhesive (e.g., a biocompatible adhesive) on the phototherapy dressing, e.g., peripheral to the island region. In some variations the semisolid medicament material (e.g., hydrogel) may be sufficiently adhesive to secure the dressing to the skin, and an additional adhesive is not necessary. However, it may be desirable to include an adhesive, particularly around the periphery of the medicament in the dressing so that the dressing acts as a vapor barrier over the treatment region of the skin.

For example, any of the phototherapy dressings described herein may be configured to have moisture vapor transmission rate (MVTR) of less than 2.3 g/m$^2$/h (grams/meter$^2$/hour). 2.3 g/m$^2$/h typically corresponds to the minimum moisture transmission rate of the skin; thus at this rate, the bandage will maintain or increase the moisture content of the skin over the treatment region. Although the support body in this region may allow water vapor to pass (although it may be treated to limit vapor passage in some variations), the proximity to the hydrogel may maintain this moist region against the skin with minimal loss of moisture from the hydrogel as a whole. Thus, in any of these variations, the dressing may act as a moisture vapor barrier.

As mentioned, the support boy may be a polymeric material arranged in a layer to be worn against the patient's skin. The layer may be relatively thin (e.g., less than 0.01 inches thick) and may be formed of a polymeric material. For example, the support body may comprise a thin layer of polyurethane or polyester, or any other material that permits the transmission of UV light (e.g., greater than 50%, 60%, 70%, 80%, 90% of the UV light in the therapeutic frequency range).

In general, the therapeutic UV light wavelength (or conversely, frequency) range may be between 295 and 330 nm, e.g., between 295 and 320 nm, between 295 and 306 nm, between 295 and 304 nm, between 295 and 302 nm, between 295 and 300 nm, between 300 and 330 nm, between 300 and 320 nm, between 300 and 315 nm, between 300 and 311 nm, between 300 and 306 nm, between 300 and 303 nm, between 303 and 320 nm, between 303 and 318 nm, between 303 and 316 nm, between 303 and 311 nm, between 303 and 306 nm, between 305 and 330 nm, between 305 and 320 nm, between 305 and 316 nm, between 305 and 309 nm, between 310 and 330 nm, between 310 and 320 nm, between 310 and 316 nm, between 315 and 330 nm, between 315 and 325 nm, between 315 and 320 nm, or any sub-region of these).

Overall, the phototherapy dressing may be relatively thin, e.g., having a thickness of less than 0.2 inches, 0.1 inches, 0.09 inches, 0.08 inches, 0.07 inches, 0.06 inches, 0.05 inches, etc., particularly over the treatment region. The dressing may be thicker in some regions than others, e.g., in the connector region configured to couple to the UV light source. In some variations the dressing includes a rim, lip, channel, ridge, etc. around the region that mates with the UV light source. This rim or lip region may prevent light from escaping when UV light is applied by the UV light source.

In general, the phototherapy dressing may have a low thermal conductivity. For example, the thermal conductivity of the dressing may be less than 0.32 W/m/° C.

As mentioned above, any of the phototherapy dressings described herein may include one or more identifiers (e.g., unique or semi-unique) identifiers that allow another device to identify the dressing and associate a particular dressing with information specific to the use of the dressing, including the composition of the dressing, the model/make of the dressing, the position of the dressing on the patient, the number of times the dressing has been treated with UV light, etc. The identifier (which may be referred to as a unique identifier) may be located on the support body and may be associated with a particular phototherapy dressing. The identifier may be a code such as a printed bar code, QR code, alphanumeric code, etc. that can be scanned or read by another device (e.g., a mobile, hand-held device and/or the UV light source). The identifier may be an RFID identifier or other electromagnetic signature/identifier. In some variations the identifier may be a chip that can transmit and/or receive information about its identity and/or operation. Thus, an identifier may be one or more of: an RFID tag, an optical code, a magnetic signature, or an alphanumeric code.

As mentioned, in any of the phototherapy dressings described herein, the dressing may include an attachment configured to releasably couple with a phototherapy UV source. For example, the attachment may be a mechanical attachment (e.g., snap, Velcro/hook and loop, clip, tie, strap, screw, button, hook, etc.) or a magnetic/electromagnetic attachment (e.g., permanent magnet, electromagnet, etc.). In some variations the attachment includes a plurality of magnets on the support body; the magnets may be positioned off-center of the dressing, e.g., around the periphery of the dressing.

Also described herein are methods of treating a skin disorder by UV phototherapy. In particular, methods of treatment include methods of treating a skin disorder such as psoriasis. Treatment methods typically include applying one or more of the dressings described above (having a medicament such as hydrogel and coal tar and/or coal tar extract) on the skin in the desired treatment sites, and applying one or more treatment doses of UV light. The treatment dose may be calculated (as described below), but may be applied for between 1 second and 20 minutes (e.g., between 1 second and 15 min, between 1 second and 12 min, between 1 sec and 10 min, between 1 min and 20 min, between 1 min and 15 min, between 1 min and 12 min, between 1 min and 10 min, etc.). The treatment does may be determined based on patient feedback (e.g., skin sensitivity) as well as characteristics of the dressing (e.g., how much UV will penetrate to skin, size of the treatment area, etc.) and characteristics of the UV source (e.g., how much energy the device will or is capable of delivering). Although any appropriate UV source may be used, example UV sources are provided herein.

For example, a method of treating psoriasis by UV phototherapy may include: attaching a dressing to a patient's skin, wherein the dressing comprises a medicament, the medicament including a hydrogel including between about 0.1% and 5.0% coal tar or car tar extract; coupling a phototherapy UV light source to the dressing; and applying UV light through the dressing from the phototherapy UV light source, including through the medicament, wherein more than half of UV light emitted by the phototherapy UV light source between 300 and 320 nm passes through the dressing.

A method of treating psoriasis by UV phototherapy may include: attaching a dressing to a patient's skin, wherein the dressing comprises a medicament, the medicament including a hydrogel including between about 0.1% and 5.0% coal tar or car tar extract; magnetically coupling a phototherapy UV light source to the dressing; detecting a unique identifier on the dressing using a hand-held device; calculating, using the hand-held device, a treatment dose of UV light; and applying the treatment dose by applying UV light through the dressing from the phototherapy UV light source, including through the medicament, wherein more than half of UV light emitted by the phototherapy UV light source between 300 and 320 nm passes through the dressing.

Any of these methods may include detecting a unique identifier on the dressing using a hand-held device. The hand-held device (e.g., smartphone, iPad, etc.) generally includes a processor and may be configured to run control logic that causes the processor to calculate treatment dosing and/or communicate (e.g., dosing information) to the phototherapy UV light source. In some variations the UF light source itself includes a processor and is capable of receiving the identifier.

In variations including a processor (e.g., in a hand-held device), the processor may be configured by control logic to calculate, using the hand-held device, a treatment dose of UV light.

As mentioned above, in any of the methods, the UV light source may be attached to the phototherapy dressing. For example, the phototherapy UV light source may be magnetically coupled to the periphery of the treatment region on the dressing. For example, applying UV light may include automatically applying a calculated treatment dose of UV light.

Any of the methods described herein may also include confirming coupling of the phototherapy UV light source to the dressing prior to applying UV light. For example the UV light source may sense or detect the attachment/coupling by a magnetic coupler.

The treatment dose may be calculated by the UV light source or by a hand-held device with a processor (e.g., smartphone), For example, a treatment dose may be calculated based on the skin type of the patient, a number of previous doses applied to the dressing, and the patient's skin sensitivity. Calculating the treatment dose of UV light may include calculating the treatment dose based on the skin type of the patient, a number of previous doses applied to the dressing, and the patient's skin sensitivity.

In general, the methods described herein typically include delivering a plurality of doses per day. These doses may be manually or automatically y applied, and (as mentioned earlier) the method may include applying UV light therapy through different dressings. In general, a dressing may also be referred to as a bandage, wrap, compress, poultice, plaster, cover, etc.

Any of these methods may include delivering one or more doses to different dressings on the body. For example, a method may include applying UV light through a second dressing on the patient's skin to deliver a second treatment dose. In some variations the delivery to multiple dressings may be used to determine dosing information, e.g., by varying the treatment does from the second treatment (compared to a first treatment dose in a different location) dose to determine a minimal erythemal dose (MED).

Also described herein are phototherapy UV light sources and systems including phototherapy UV light sources and/or phototherapy dressings, as described briefly above. The phototherapy UV light source and the phototherapy dressing may be configured (e.g., with complimentary connectors) to couple together. In general, the UV light sources described herein include a one or more LEDs or other sources of UV light. For example, the phototherapy UV light source described herein may include a plurality of UV emitting LEDs (e.g., 18 LEDs arranged in a 3×6 array within a 2 inch by 1 inch rectangle).

For example, a system for treating skin disorders by UV phototherapy, may include: a phototherapy dressing comprising a support body, and a medicament in communication with body, the medicament including a hydrogel having between about 0.1% and 5% coal tar or car tar extract, wherein the body and medicament occlude less than 50% of UV light at wavelengths between 300 and 320 nm from passing through the phototherapy dressing; and a phototherapy UV light source configured to emit UV light at an intensity of greater than 2 mW/cm$^2$ at a wavelength between 300 and 320 nm, and a connector configured to magnetically secure the phototherapy UV light source to the phototherapy dressing.

A system for treating skin disorders by UV phototherapy may include: a phototherapy dressing comprising a support body, and a medicament in communication with body, the medicament including a hydrogel having between about 0.1% and 5% coal tar or car tar extract, wherein the body and medicament occlude less than 50% of UV light at wavelengths between 300 and 320 nm from passing through the phototherapy dressing; a phototherapy UV light source configured to emit UV light at an intensity of greater than 2 mW/cm$^2$ at a wavelength between 300 and 320 nm, and a connector configured to secure the phototherapy UV light source to the phototherapy dressing; and control logic configured to determine a treatment dose, wherein the control logic is configured to control application of the treatment dose by the UV light source.

As mentioned any of these systems may include control logic configured to determine a treatment dose, wherein the control logic is further configured to control application of the treatment dose by the UV light source. The control logic may generally be a non-transient computer readable storage medium that controls the operation of the processor on which it is operating to regulate and monitor the processor and device (e.g., phone), including to calculate therapeutic dose.

Any of the systems described herein may include a safety circuit configured to prevent the phototherapy UV light source from emitting UV light unless the phototherapy UV light source is coupled to the phototherapy dressing. The phototherapy UV light sources may also generally include an extension or skirt region around the light-emitting portion, to prevent spill-over of UV light when it is being applied to a patient's lesion.

As mentioned, the phototherapy dressing may include one or more magnetic couplers configured to couple with the connector of the phototherapy UV light source. In addition, the phototherapy UV light source may include a thermistor, and the phototherapy UV light source nay be configured to limit the delivery of UV light based on the thermistor.

The control logic referenced above may determine treatment dose based on one or more of: a type of disease, a skin type, a patient feedback on skin sensitivity, a previous dose history, an amount of UV light absorbed by the dressing, an edge detection for recognition and guidance of the UV light, an amount of induration, an amount of scale, an amount of redness, a location of the lesion, and a thickness of epidermis. The control logic may be configured to determine the treatment dose based on a center of the wavelengths emitted by the UV light source. For example, the light wavelength claimed as the therapeutically relevant range may be centered at less than 306 nm (e.g., less than 305 nm, less than 304 nm, less than 303 nm, less than 302, etc.) and has a full width half power of less than 30 nm, 25 nm, 20 nm, 18 nm, 15 nm, etc. In some variations, the starting treatment dose is less than 132 mj/cm$^2$.

Although the dressings above (and descried herein) may include a support body (which may include attachment sites for the UV light source), in some variations the apparatus includes just the hydrogel, which may be applied the body directly. For example, described herein are hydrogels that may be mixed with a therapeutic (e.g., coal tar, coal tar extract) and applied to the skin.

For example a hydrogel (which may be used with a phototherapy procedure) may include: water in a concentration between 90 and 99.9%; and coal tar or coal tar extract between 0.1 and 5% by weight/volume; wherein the hydrogel occludes less than 50% of UV light at wavelengths between 300 and 320 nm.

BRIEF DESCRIPTION OF THE DRAWINGS

FIGS. 3A-3C illustrate three embodiments of a system for treating skin disorders by ultraviolet phototherapy.

FIG. 6 illustrates a method for determining a therapeutic dose of light.

Figure 1A:
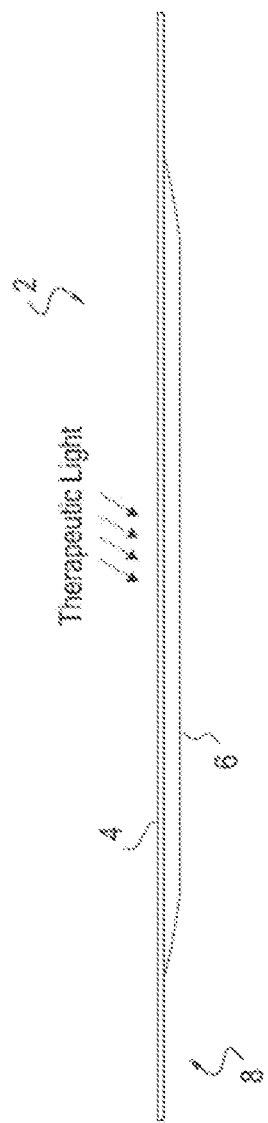
FIGS. 1A-1B illustrate one embodiment of a dressing that may be used with a phototherapy system.

Figures may are not shown to scale unless otherwise indicated.

DETAILED DESCRIPTION

The following description of the preferred embodiments is not intended to limit the invention to these preferred embodiments, but rather to enable any person skilled in the art to make and use this invention.

Phototherapy apparatuses (including systems and devices), and related methods are provided herein, including, but not limited to: phototherapy dressings for concurrent delivery of a medicament (e.g., coal tar and/or coal tar extract in a hydrogel); medicaments including a hydrogel and coal tar and/or coal tar extract that may be used alone or with a dressing; phototherapy UV light sources capable of operating with the phototherapy dressings and/or medicament; control logic for determining therapeutic dosing and/or controlling the phototherapy UV light source; and methods of using any of these. In general, these apparatuses and methods may be used to deliver therapeutic energy to a person. Although the majority of examples provided herein are for the delivery of light energy, e.g., UV (including narrow band UV) light, the methods and apparatuses described herein may also be used with other energy modalities, including other electromagnetic radiation waves, such as infrared light, blue light, radiofrequency waves, and magnetic energy, as well as non-electromagnetic energy such as ultrasound, or any other type of therapeutic energy. For example, the methods and apparatuses described herein may be used to apply therapeutic ultrasound may be used to treat ligament sprains, muscle strains, bursitis, tendonitis, joint inflammation, plantar fasciitis, metatarsalgia, facet irritation, impingement syndrome, rheumatoid arthritis, osteoarthritis, teeth, bone, myofascial pain, and/or scar tissue adhesion. Radiofrequency therapy may be used to treat tumors, cardiac arrhythmias, chronic and postoperative pain, bone fractures, and soft tissue wounds.

Therapeutic UV light may be used to treat a skin disorder or disease. For example, psoriasis, eczema, vitiligo, acne *vulgaris*, neonatal jaundice, atopic dermatitis, acute forms of dermatitis, lichen planus, or any other skin disorder or disease may be treated by the systems and methods disclosed herein. Alternatively or additionally, therapeutic UV light may be used to treat depression, jaundice, seasonal affective disorder, fibromyalgia, patients that are phase delayed, cancer (photopheresis), chronic ulcers, rheumatoid arthritis, osteoarthritis, tendinopathy, chronic joint disorders, and periodontitis. In particular, described herein are methods and apparatuses for treating skin disorders such as psoriasis.

A patient (e.g., a person or subject) and/or clinician (doctor, nurse, assistant, medical technician, etc.) may use the systems and methods described herein at home, in a clinic, in a hospital, in a vehicle, or in any other location.

Dressing

The medicaments described herein may be specifically formulated for the application of energy (such as UV energy) concurrent with the delivery of a topical therapeutic agent (e.g., coal tar, coal tar extract, etc.). In particular, the medicament may be configured so that it is largely transparent to the to the applied energy modality. For example, a medicament for use with the delivery of UV energy may include a semisolid substance (e.g., a suspension, a colloid, etc.) into which the medicament has been added at an appropriate therapeutic level. The medicament may include, for example, a hydrogel (having a high water content, e.g., between 90 and 99.9% water), and a medicament such as coal tar and/or coal tar extract (e.g., between 0.1 and 5% by weight/volume). The medicament may be configured to occlude less than a target percent of the UV light transmitted through it (e.g., when applied to a skin surface, including as part of a dressing). The amount of UV transmission through the medicament may be controlled by controlling the composition (e.g., percentage of coal tar and/or coal tar extract, typically between 0.1% and 10%, more preferably between 0.1% and 5%), thickness (e.g., between about 0.01 inches to 0.1 inches thick, e.g., between about 0.01 inches and about 0.08 inches thick, etc.). When applied as part of a dressing, the medicament may be applied onto a surface of the dressing, such as a thin support or support body, so that a portion of the dressing (support body) partially covers one side of the medicament; the other side may contact the patient's skin. In some variations the dressing may include an opening so that the support body does not cover the medicament, and therefor doesn't occlude the UV light transmission in this region. In variations in which the support body of the dressing is in the path of the UV light (e.g., between the UV light source and the skin) in addition to the medicament, this portion of the dressing may be relatively UV light transparent in the therapeutic frequency of UV light to be applied, so that the total UV light transparency through the dressing including the medicament is greater than a predetermined minimum threshold, such as 20%, 30%, 40%, 50%, 60%, 70%, 80%, 90%, etc. For example, to deliver a dose of UV energy within the therapeutic range of about 295-330 nm (e.g., 300-320 nm or any other sub-range within 295-330 nm) over a reasonable amount of time using a phototherapy UV light source, including those described herein, the minimum percentage of UV light transmitted through the dressing (including any intervening support body of the dressing surface and the medicament) may be about 40% (or about 45%, about 50%, about 55%, etc.) where each therapeutic does last for between about 1 minute and 20 minutes (e.g., 5 min-15 min, 10 min-20 min, etc.). For example, when the dressing includes a medicament comprising a hydrogel and between about 0.1 and 5% coal tar or coal tar extract, and the medicament is about 0.01 inches to 0.08 inches thick (where thickness is the direction normal to the skin), and the dressing also includes a thin support layer (support body) formed of a polymeric material (e.g., polyurethane) that is less than 0.005 inches thick, the dressing may occludes less than 50% of UV light at wavelengths between 300 and 320 nm.

Figure 1B:
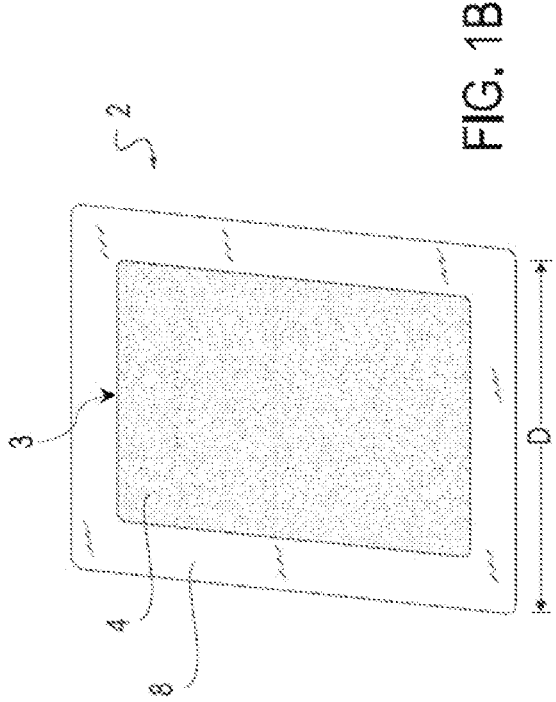

FIGS. 1A and 1B illustrate one embodiment of a dressing 2 for use with a phototherapy system. This dressing 2 may be used to treat a condition such as a skin disorder (e.g., skin disease, etc.). The dressing may be used in concert with a therapeutic energy-delivering device as described below, but it may also be used independently for therapy, including for wound healing, skin treatment, or any suitable applications, clinical or otherwise. A dressing 2 for use with a phototherapy procedure may include a body 4, a medicament 6, and an adhesive 8.

In one embodiment, a dressing for use with a phototherapy system includes a body 4, as shown in FIGS. 1A and 1B that is flexible and planar. The shape of the body may thin, particularly over the medicament 6, though it may be thicker in other regions. For example, the region of the support body over the medicament may be less than 0.009 inches thick (e.g., less than 0.008 inches, less than 0.007 inches, less than 0.006 inches, less than 0.005 inches, less than 0.004 inches, less than 0.003 inches, less than 0.002 inches thick, etc.). In some embodiments, the dressing includes a medicament as described above, such as a hydrogel, a low or high durometer silicone, urethane, other flexible polymers, a hydrocolloid, or a combination of one or more of these materials. The medicament may be attached to the body of the dressing, or separately applied to the skin so that the dressing may be applied over it. When the medicament is attached, the medicament for UV phototherapy may include a hydrogel and a therapeutic agent such as (but not limited to) coal tar (and/or coal tar extract) at a therapeutic concentration (such as between about 0.1% and 10%, e.g., 0.1% and 5%, etc.). As mentioned, the dressing, including the body and the medicament, may be configured to occlude less than a predetermined amount (e.g., 50%) of UV light at wavelengths within a therapeutic range (e.g., between about 300 and 320 nm). For example, the dressing may occlude less than 40%, 30%, 20%, 10%, or 1% of UV light at wavelengths between 300 and 320 nm. In one embodiment, the dressing occludes no (i.e., 0%) or approximately no UV light. In some embodiments, the dressing may occlude less than 50% of UV light at wavelengths between 250 and 400 nm or any sub-range there between; for example, the dressing may occlude less than 50% of UV light at wavelengths between 250 and 300 nm, 300 and 350 nm, or 350 and 400 nm.

In FIGS. 1A and 1B, a dressing 2 that may be used with a phototherapy system includes a medicament 6. The medicament may decrease dryness, decrease skin scaling, increase dead skin cell shedding, decrease itchiness, and/or increase/decrease any other property of the skin or underlying tissues. In general, the medicament may include a pharmaceutical agent (therapeutic agent); in some embodiments, the medicament may comprise a homeopathic or non-medicated therapy or salve. A medicament may include, for example, an agent such as a hormone, an antibiotic, an antimicrobial, an anti-fungal, an anesthetic, an antiseptic, an anti-inflammatory, antihistamine, an analgesic, an acne medication, an anti-aging compound, a moisturizer, a hair growth promoter, a hair growth preventer, a skin growth promoter, a cleanser, or any other beneficial substance. In some embodiments, the medicament may include coal tar, coal tar extract, corticosteroids, salicylic acid, anthralin (dithranol), cade oil, vitamin D analogues (e.g., calcipotriene, anthralin, tazarotene, calcitriol), steroids, psoralen, aloe vera, jojoba, zinc pyrithione, capsaicin, acetic acid, urea, phenol, or any other medicament known to one skilled in the art to be therapeutic or helpful for topical treatment (and particularly topical treatment in conjunction with a phototherapy or other energy-application therapy). Even agents, such as coal tar and/or coal tar extract that are known to significantly occlude UV light may be incorporated into a phototherapy medicament and/or dressing; as described herein, such active agents may be prepared as described herein so that the resulting dressing with medicament does not significantly occlude therapeutic light (e.g., occludes less than 50%, 40%, 30%, 20%, 10%, or 1%).

As described above, of particularly interest for UV phototherapy applications, a medicament may include a hydrogel and coal tar and/or coal tar extract. For example, the medicament may include between about 0.01% and 10% coal tar or coal tar extract.

Alternatively, the medicament may include between about 0.001% and 0.01%, 0.01% and 0.1%, 0.1% and 0.5%, 0.5% and 1%, 1% and 1.1%, or any other percentage. In some embodiments, the medicament may absorb less than 40%, 30%, 20%, 10%, or 1% UV light at wavelengths between 300 and 320 nm. In some embodiments, the medicament absorbs no or substantially no UV light at wavelengths between 300 and 320 nm. In one embodiment, the medicament absorbs less than 50% of UV light at wavelengths between 300 and 320 nm. In some embodiments, the medicament may absorb less than 40%, 30%, 20%, 10%, or 1% UV light at wavelengths between 250 and 400 nm or any sub-range there between; for example, between 250 and 300 nm, 300 and 350 nm, or 350 and 400 nm.

In some embodiments, as shown in FIGS. 1A and 1B, a dressing 2 may include an adhesive 8, The adhesive may function to couple, adhere, attach, or otherwise fasten a dressing to a patient's skin. In sonic embodiments, the adhesive 8 is positioned on a peripheral region of the dressing. For example, in some embodiments, the medicament 6 is bordered on one or more sides of its perimeter by the adhesive 8. In some embodiments, the dressing 2 is formed of a body layer 4, an adhesive layer 8, and a medicament layer 6, In some such embodiments, the adhesive layer 8 and the medicament layer 6 are each coupled to a bottom (i.e., skin interfacing) surface of the body layer 4, and the adhesive layer 8 is disposed around the medicament layer 6 the medicament may be in a contacting or non-contacting arrangement with the adhesive). In FIG. 1B, the adhesive layer 8 circumscribes the medicament layer 6, forming an island region 3 within Which the medicament is positioned. In some embodiments, the medicament 6 is a layer having a diameter (D) or length, width, thickness, and surface area. This surface area may be less than the surface area of the adhesive 8. In one embodiment, the dressing includes adhesive 8 at least on a peripheral region of the support body 4 configured to secure the support body 4 to a patient's skin. In some embodiments, the adhesive 8 may be a thin film to improve conformation to a patient's body. In some embodiments, to improve comfort, the dressing may include a thickness of less than 3, 2.5, 2, 1.5 1, 0.5, or 0.25 cm. In one embodiment, the dressing includes a thickness of less than 0.5 cm. Thus, the medicament layer and adhesive layer may have a thickness that is thinner than the overall thickness of the dressing.

A mentioned, in general a medicament may be formed of, or otherwise includes, a semisolid substance with a viscosity greater than water (i.e., greater than $8.90 \times 10^{-3}$ dyn·s/cm² at about 25° C.). For example, the medicament may be formed of or include a hydrogel layer. The hydrogel typically includes water at a concentration between 0.1% and 99.9% or any sub-range there between, e.g., between about 10% and 99.9%, 20% and 99.9%, 30% and 99.9%, 40%, and 99.9%, 50% and 99.9%, 60% and 99.9%, 70% and 99.9%, 80% and 99.9%, 90% and 99.9%, 95% and 99.9%, or 97% and 99.9%.

Figure 1C:
FIG. 1C illustrates one variation of a hydrogel that may that may be used with a phototherapy system as described herein.

In some variations the medicament (e.g., hydrogel with therapeutic agent) may be used without a dressing, e.g. by itself. For example, FIG. 1C illustrates a hydrogel that may be used with a phototherapy system. In this example, the hydrogel 7, includes coal tar (and/or coal tar extract) within the gel. This gel may be formed into a relatively thin layer (e.g., between about 0.1 inches to about 0.01 inches that is applied to the skin. The hydrogel may be sufficiently adhesive (tacky) to be secured without the need for an additional adhesive, or an additional adhesive material may be used (e.g., around the periphery). When used with a UV phototherapy light source, such as those descried herein, it may be placed over the hydrogel (and in some cases against the hydrogel) or over the skin surrounding the hydrogel. In general, a hydrogel may include water in a concentration between 0.001% and 10%, 10% and 20%, 20% and 30%, 30% and 40%, 40% and 50%, 50% and 60%, 60% and 70%, 70% and 80%, 80% and 90%, or 90% and 99.9%.

As mentioned, the dressing may be configured to have a moisture vapor transmission rate of less than the skin or less than 2.5, 2.25, 2.0, 1.75, or 1.5 g/m²/h (grams/meter²/hour). In one embodiment, the dressing has a moisture vapor transmission rate of less than 2.4 g/m²/hour. Increased moisture levels may increase the transparency of the skin to therapeutic light and decrease the thickness of the epidermis, allowing light to reach deeper and have an increased therapeutic effect. Although any of the dressing described herein may be configured to include a material (and/or coating, layer, etc.) that has a low moisture transmission rate, such an additional component may not be necessary, particularly when the dressing includes a hydrogel having a relatively large percentage of water.

In some embodiments, the dressing may increase the local temperature and reduce the proliferation of skin cells under the dressing. The dressing may function as an insulating layer, or the dressing may include an increased thickness for improved insulation. In some embodiments, the dressing may include a thermal conductivity of less than skin or less than 0.50, 0.40, 0.35, 0.30, 0.25, or 0.20 W/m/° C. In one embodiment, the dressing may include a thermal conductivity of less than 0.32 W/m/° C.

A dressings may have any appropriate shape, for example a triangle, rectangle, square, circle, or hexagon, for enabling full coverage of any lesion size or shape. The dressing may be any appropriate size. For example the dressing may have a (planar) width or diameter dimension, referred to herein as a diameter D and depicted in FIG. 1B, of less than 20, 15, 10, 5, 4, 3, or 2 inches to minimize the amount of unaffected skin that is treated. By minimizing the dimensions of the dressing, the dressing may cover a minimum amount of healthy skin. Alternatively, for larger lesions, multiple dressings may be positioned on the skin adjacent to each other. The dressing may be marked or printed, including fiduciary markers for alignment with a UV light source, and may also include one or more identifiers, as described below.

In some embodiments, an outer edge of the body of the dressing (excluding the thin adhesive film border) may have the same dimension as an inner edge of a UV light source (described in more detail below), such that accidental detachment due to shear force may be reduced. Further, in some embodiments, the outer edge of the body of the dressing may be thin, compared to more centrally located regions (even on the peripheral region), reducing risk of accidental failure from shear forces.

As mentioned, and of the variations described herein may include one or more identifiers, including unique identifiers. FIGS. 2A-2D illustrate four embodiments of unique identifiers 10 of a dressing 2. A unique identifier may be correlated with one or more of: dressing type, number of uses (e.g., 1, 2, 3, 4, 5, 6, 7, 8, 9, 10, greater than 10), manufacturer, purchase date, serial number, indication, prescription, patient name, dressing absorption of UV light, or any other information relevant to the dressing, patient, or indication. The unique identifier refers to the ability of the identifier to correlate information with a particular dressing on a particular patient. The dressing identifier may be made unique when associated with the particular location it is applied on a particular patient.

Figure 2A:
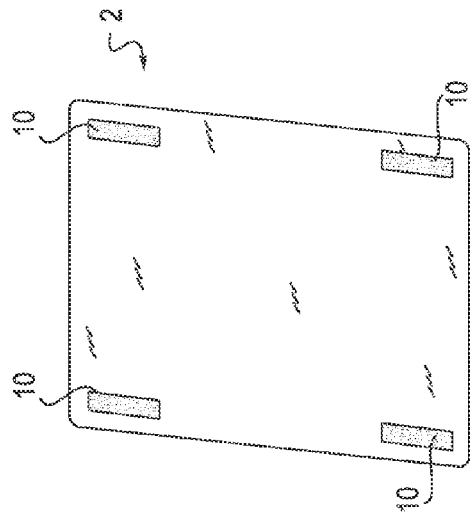
FIGS. 2A-2D illustrate four embodiments of unique identifiers of a dressing.
Figure 2B:
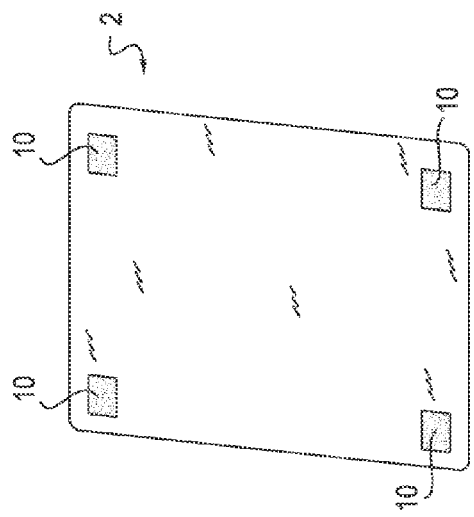
Figure 2C:
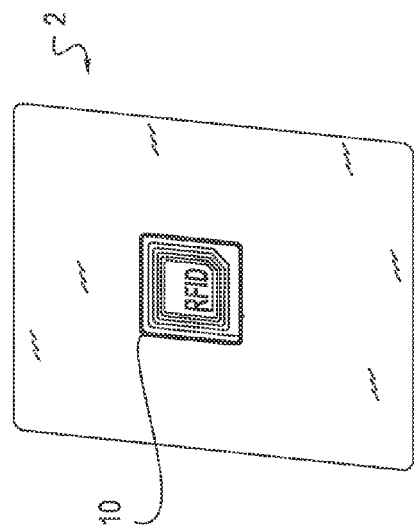
Figure 2D:
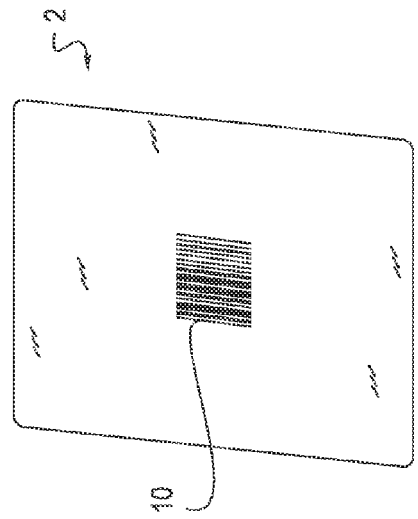

A unique identifier 10 may be designed, sized, and positioned to minimize blocking of therapeutic light. For example, a unique identifier may be completely transparent to therapeutic light or may be located on a dressing on the periphery of the outside of the dressing or substantially outside of the body of the dressing where therapeutic light is directed (e.g., FIG. 2B). In some embodiments, a unique identifier may include RFID (e.g., FIG. 2C), a near field communication (NFC) chip (e.g., FIG. 2C), an optical code (e.g., q-code; FIG. 2D), a universal product code (UPC) (e.g., FIG. 2D), a magnet with a unique magnetic field (e.g., FIG. 2A), an infrared (IR) reflective strip (e.g., FIG. 2B), a giant magnetoresistance, or any other identifier known to one skilled in the art. In one embodiment, the unique identifier 10 includes a magnet or series of magnets configured to induce a specific magnetic field based on a ferromagnetic material coupled to the magnet or series of magnets, as shown in FIG. 2A. For example, the ferromagnetic material coupled to the magnet may include stainless steal, iron, nickel, cobalt, neodymium, samarium-cobalt magnets, or any other ferromagnetic material. In some embodiments, the magnets may be positioned as far away from the center of the dressing and/or each other as possible to minimize moments and accidental disconnection of the light from the dressing, for example from shear, peeling, and/or pull forces.

In some embodiments, the dressing may include multiple unique identifiers that, when combined, create a unique code for each dressing. For example, the presence or absence of multiple magnets detectable by a Hall Effect sensor or reed switch on the light (described below) could form a binary code that is used to create an identifying code for a dressing. This code may then be used to recognize a dressing during therapeutic use. For example, a device, such as the light source described below, may be configured to read the code when it is initially coupled to the dressing and store the code for subsequent uses of the dressing.

A unique identifier may be read by a device. For example, the unique identifier may be read by a mobile device, handheld device (e.g., smartphone), scanner, computing device, light source (e.g. UV light source), or any other type of device capable and configured to read it, e.g., having a reed switch, Hall Effect sensor, or any other type of switch or sensor. In one embodiment, the unique identifier may be read by a handheld light source, for example a UV light source, comprising a Hall Effect sensor, as will be described in further detail below. The identifier may be encoded (e.g., to protect patient privacy), so that only approved (e.g., paired) devices are able to read the information encoded.

One or more dressing may be included in a kit with multiple dressings; in some variations, each dressing includes a unique identifier. In some variations, each dressing may include the same identifier or a different identifier. Each dressing in a kit may include a different medicament and be configured to be delivered in a multi-step process. For example, the first dressing may descale, the second dressing may be configured to decrease cellular product, the third dressing may be configured to photosensitize the skin, and the fourth dressing may be configured to increase penetration.

As mentioned above, a medicament may include any appropriate therapeutic agent, including (but not limited to) one or more of: coal tar, coal tar extract, corticosteroids, salicylic acid, anthralin (dithranol), cade oil, vitamin D analogues (e.g., calcipotriene, anthralin, tazarotene, calcitriol), steroids, psoralen, aloe vera, jojoba, zinc pyrithione, capsaicin, acetic acid, urea, phenol, or any other medicament known to one skilled in the art. In the context of the medicaments and dressings described herein, these agents do not significantly occlude UV light when included in the dressing.

A kit may include one or more reusable dressings as well as one or more thin films with waterproof adhesives for re-attaching the dressing to the skin.

As described in greater detail below, and of the dressing described herein may include a connector configured to connect (e.g., specifically, securely and releasably connect) to an energy applicator such as a phototherapy UV light source. The connector may be mechanical, electromagnetic, chemical, or the like, and may be located anywhere on the dressing, including in particular, regions peripheral to the region over the medicament when applied to a patient's body.

Any of the medicaments and/or dressing described herein may be used as part of a system including an energy applicator, such as a phototherapy UV light source. For example, FIGS. 3A-3C illustrate three embodiments of systems for treating skin disorders or other health conditions by ultraviolet phototherapy. A system for treating skin disorders or other conditions by UV phototherapy may include a dressing 2, a UV light source 12, and control logic (e.g., operating a general or dedicated processor and configured to control a computing device 28 and/or light source 12). The dressing 2 may be adapted to occlude less than a threshold level of UV light (e.g., 50% of UV light at wavelengths between 250 and 400 nm, e.g., between 300 and 320 nm), as described above. In some embodiments, the dressing may include a first connector 14a. The system may include a UV light source 12 configured to emit UV light at an intensity of greater than 2 mW/cm$^2$ at a wavelength between 300 and 320 nm. Further, the UV light source 12 may include a second connector 14b configured to couple to the first connector 14a on the body. The system may additionally or alternatively include a control logic configured to determine a treatment dose, and in various embodiments, the control logic controls application of the treatment dose by the UV light source 12. As mentioned above, a hydrogel instead of a dressing may be used with a phototherapy system. A hydrogel may include water in a concentration between 0.001% and 10%, 10% and 20%, 20% and 30%, 30% and 40%, 40% and 50%, 50% and 60%, 60% and 70%, 70% and 80%, 80% and 90%, or 90% and 99.9%.

In some embodiments, a system for treating skin disorders by UV phototherapy functions to deliver UV light to a portion of skin that is affected by a skin disorder, for example psoriasis, but alternatively, the system may be used in any suitable application, clinical or otherwise.

Also described herein are phototherapy UV light sources. In general, a phototherapy UV light source include one or more UV light emitter (e.g., LED, CFL, etc.) that is configured to emit (and in some cases specifically emit) UV light in the target wavelength range (e.g., 300-320 nm, etc.). The phototherapy device may also include a power source (e.g. battery, long-lasting capacitor, etc.), a controller (e.g., circuitry connected to the power source and UV light emitter to control operation of the device), which may include one or more clock/timer and a communications circuit (e.g., wireless communication circuit, such as Bluetooth, WiFi, ultrasound, etc.). The UV light source may also include a protective shroud or cover for mating with the patient's skin and/or the dressing. The UV light source may also include one or more connectors for coupling with the dressing as described herein. In some variations the UV light source also includes a reader for reading an identifier on a dressing. A UV light source may also include one or more indicators (including non-UV light emitters) to indicate when the device is in operation (e.g., when the UV light is on); the indicator may be visible on an outer surface of the phototherapy UV light source device and/or it may shine light with the UV light (e.g., into a shroud or cover region), so that the user can visually identify when the UV light is on. Any of these devices may also include safety circuitry and/or logic configured to disable the emission of UV light when not connected to the patient and/or a dressing.

As shown in FIGS. 3A and 3B, a system for treating skin disorders or other health conditions by ultraviolet phototherapy may include a phototherapy UV light source 12 (also referred to as a simply a UV light source). The UV light source 12 functions to couple to the dressing 2 and to deliver UV light through the dressing to a target, such as a skin lesion 30, on a patient. In some embodiments, the light source 12 may include a light emitting diode (LED), a compact fluorescent lamp (CFL), an arc lamp, or any other type of light source. In one embodiment, the light source includes one or more LEDs 26. In some embodiments, the UV light source is configured to emit UV light at an intensity of greater than 1, 2, 2.5, 3, or 3.5 mW/cm$^2$. In some embodiments, the UV light source is configured to emit UV light at a wavelength between 300 and 320 nm. In one embodiment, the UV light source emits UV light at an intensity of greater than 2 mW/cm$^2$ at a wavelength between 300 and 320 nm. In some embodiments, the UV light source emits UV light at a wavelength between 250 and 400 nm or any sub-range there between, such as 250 and 300 nm, 300 and 350 nm, or 350 and 400 nm. In one embodiment, the UV light source emits UV light at a wavelength between 300 and 320 nm.

As shown in FIGS. 3A and 3B, the UV light source may include a battery 16 (and/or a port or other connection to a secondary device, for example, a mobile device for power), a controller 18 which may include a microprocessor and memory (e.g., ASIC) with the control logic stored thereon, a Bluetooth antenna or other wireless technology (e.g. infrared or near-field communication beacon) 20 or a hard-wired connection (e.g., FireWire IEEE 1394, universal serial bus) for communicating with a separate and/or second controller 28, such as a mobile device, a sensor 24 for reading one or more unique identifiers, and/or a shield 22 for increasing focus of the UV light to the dressing and reducing exposure of unintended areas to the UV light. In some embodiments, the control logic of the UV light source determines and controls the settings and functionality of the light. In other embodiments, the separate controller 28, additionally or alternatively determines and controls the function of the light. The wireless communication may be done with near infrared, Wi-Fi, or Bluetooth. Additionally or alternatively, as shown in FIG. 3B, the light source may include a camera 38 for identifying the edges of the lesion, in order to facilitate proper positioning of the dressing and/or light source over the lesion.

In some embodiments, the controller may vary the initial UV light administered to different lesions to more quickly determine a minimal erythemal dose (MED) for different parts of the body and/or to determine an ideal MED for the patient. In some embodiments, the MED may be determined based on feedback from the patient. Additionally or alternatively, a controller may provide multiple doses in a day, such that an MED is not exceeded and/or the patient does not experience redness, burning, itching, or induration.

Any of the apparatuses described herein may also include control logic for controlling the application of energy and/or for determining a therapeutic dose, therapeutic regimen and/or for monitoring the application of the therapy. The control logic may generally be hardware, software, firmware, or some combination thereof. For example, in some embodiments, a mobile device 28 in communication with the light source 12 may include an application ("app") that configures the mobile device (e.g., smartphone) to operate as the control (e.g., running the control logic). In such embodiments, the mobile device 28 may include a processor and memory with instructions for the app's graphical user interface stored thereon. The memory may further include additional instructions for interacting with the controller and for processing data received from the controller 18. In various embodiments, both the mobile device 28 and the controller 18 include a wired or wireless connection to enable two-way communication between the devices. In at least some embodiments, the mobile device 28 is also in wireless communication with a remote application server, which stores additional instructions and/or databases and is configured to transmit data to, and receive data from, the mobile device 28. In various embodiments, biographical information about a user (i.e., user profile information) and data about past use (e.g., data and time of application, treatment dosage applied, and documented photographs) are stored within the server.

In some embodiments, the app may allow the patient to input information to determine his/her Fitzpatrick skin type and use this information to tailor the initial dose of light to the patient. Fitzpatrick skin type is determined by answering a series of validated questions about eye color, hair color, skin color, freckles, and/or skin reaction/sensitivity to sun and sun exposure. The app may remind the patient to deliver the therapy on a regular basis and display a visual image or chart of the amount of energy delivered to each lesion. A patient may use the phone camera through the app to identify a lesion on the patient's skin and to record where the lesion is on his/her body and track progression of the lesion. Further, a patient may use the phone camera through the app to take a picture of a temperature and/or UV light sensitive color-changing strip to determine the amount of energy to deliver to the patient's skin to avoid damage. The app may take a picture of the lesion during therapy and then display images of each lesion over time to the patient or post to a social network (e.g., to penalize patients for missing an application, reward patients for delivering an application, allow patients to share success stories and tips for usage).

The UV light source 12 may couple to a dressing 2 and/or to the patient. For example a UV light source may couple to the patient and/or dressing using one or more of: a strap that wraps around the patient's body, a re-usable pressure sensitive adhesive, single use adhesive strips, one or more magnets, one or more electromagnetics, one or more ferromagnetic materials, sub-atmospheric pressure (e.g., generated from a suction unit), a mechanical connection (e.g., snaps, Velcro, zipper, buttons), or any other coupling mechanism. In one embodiment, as shown in FIG. 3A, the light source includes a second connector 14b comprising, for example a magnet, for coupling to a first connector 14a, for example a magnet, on the dressing 2. Additionally or alternatively, as shown in FIG. 3C, the second connector 14b on the light source 12 may be secured to the light source by a holder 15. The holder 15 may include at least one wall, such that the holder 15 surrounds and secures the second connector 14b to the light source. In some embodiments, a plurality of walls substantially surrounds the second connector 14b on all sides. At least one of said walls may include an aperture 17. The aperture 17 in the wall of the holder 15 may be sized and configured for receiving the first connector 14a (located on the dressing), such that the first and second connectors are in direct contact to maximize an attraction, for example magnetic attraction, and/or a contact surface area between the first and second connectors. The light source 12 may detect the coupling of the light source to the dressing or the proximity of the light source to the dressing. In some embodiments, the detection of the coupling between the dressing and the light source triggers a safety circuit that allows for therapeutic light to be delivered only when attachment or proximity to the dressing is detected.

Further, the light source 12 may optionally include an apron, shield, or safeguard 22 to reduce or prevent accidental use of the light and/or exposure of tissue that is not under a dressing. In some embodiments, the apron, shield, or safeguard 22 may include smart glass or switchable glass, such that it blocks the UV light from reaching the healthy skin. Further, the shield 22 may include a compressible and/or displaceable section or portion, such that the shield may conform to curved surfaces of the body. The compressible portion may include a reticulated open cell foam with multiple layers of varying stiffness. Alternatively, the compressible portion may include a displaceable low durometer silicone that is UV transparent. In some embodiments, the curved surface of the body may be detected by the shield, for example using a 3D scan of the body surface. Further, in some embodiments, the shield 22 may be configured to focus light across an aperture plane. For example, the light shield may include a high efficiency diffuse reflector or elliptical shape to distribute light equally across the aperture plane or have a non-continuous shape to fit within an external structure.

Any of the systems for treating skin disorders by UV phototherapy described herein may include control logic. In some variations the control logic determines a treatment dose and/or regimen of UV light based on one or more of: disease type, a skin type, a patient feedback on a sensitivity of a lesion or group of lesions, a previous dose history, an amount of UV light absorbed by the dressing, an edge detection for recognition and guidance of the UV light, an amount of induration, an amount of scale, an amount of redness, a location of the lesion, and/or a thickness of the epidermis, as shown in FIG. 6. Further, the control logic may (in some variations) control the application of the determined dose by the UV light source. For example, the light source may deliver a narrowband of UV light at a wavelength between 300 and 320 nm, and in some embodiments, the closer the wavelength gets to 300 nm, the smaller the half power full width power will be to minimize the amount of light below 300 nm which is not therapeutically effective. Further, the closer the wavelength gets to 300 nm, the more the dose of light may be decreased. For example, in some embodiments, the dose of UV light determined by the control logic depends on the center of the light wavelength. As one example, a wavelength with a center or average at 310 nm induces the maximum dose, while a wavelength of 304 nm or any wavelength less than 304 nm induces a dose of less than half the dose given at 310 nm. In some embodiments, the center of the light wavelength is held at a value or varied between a plurality of values each greater than 296 nm. As another example, a wavelength with a center or average of less than 306 nm has a full width half power of less than 30 nm and a treatment dose of less than 130 mj/cm$^2$, where 130 mj/cm$^2$ is based on an MED recommended minimum dose for narrowband UVB light treatment by the American Academy of Dermatology.

A system for treating skin disorders by UV phototherapy may include a dressing labeling system. The dressing labeling system may function to differentiate different parts of the body or other use specifications, such that each label may be read by a light source and indicate, for example a location, indication, date, number of uses, and/or any other information. By grouping the dressing by region of the body, the dosing for a region of the body can be grouped to simplify the number of identifiers needed for the body. For example, if the body may be divided into three regions: trunk, above elbows and knees, and below elbows and knees, a person who has multiple lesions on different parts of their body may only need three types of dressing and may only need to enter in sensitivity to previous days' treatment one time. Alternatively, the body could be divided into 5 regions: trunk to knees and elbows, knees, below knees, elbows, and beyond elbows.

Figure 4C:
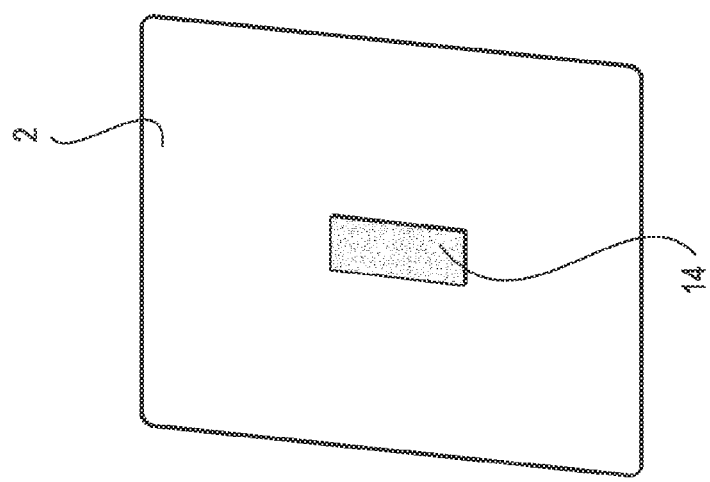
FIGS. 4A-4C illustrate two embodiments of a dressing with connectors for alignment with a light source.
Figure 4B:
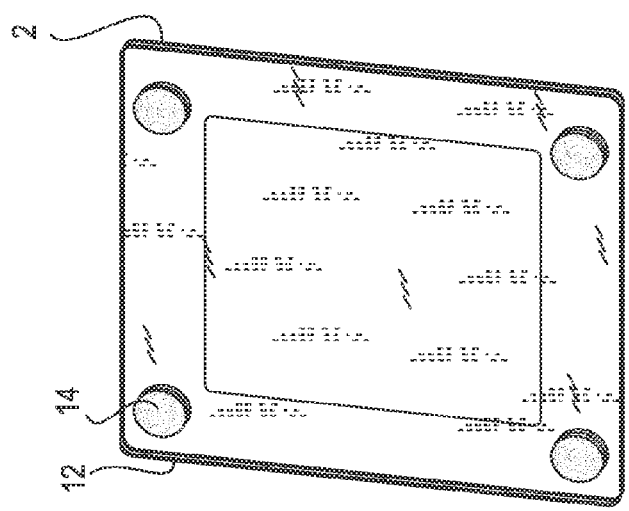
Figure 4A:
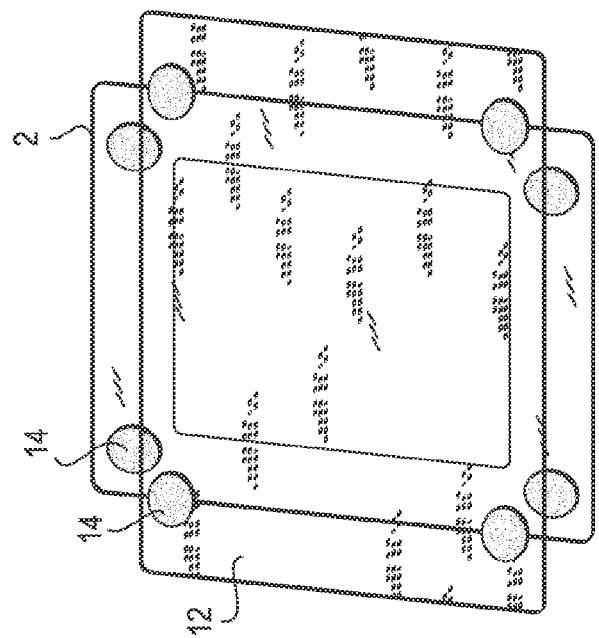

FIGS. 4A-4C illustrate two embodiments of a dressing 2 with connectors 14 for alignment with a light source 12. As shown in FIGS. 4A-4C, a dressing 2 may include one or more connectors 14 for coupling and aligning with a light source 12. In some embodiments, the connectors 14 in the dressing 2 may include one or more magnets. For example, the magnets may include neodymium, iron boron (e.g. NDFeB, NIB), samarian cobalt (SmCo), electromagnets, or ferromagnets. In some embodiments, as shown in FIG. 4A, the connectors of the dressing 2 and light source 12 may be misaligned in a first configuration to limit connectivity and inhibit delivery of therapeutic light; in a second, rotated configuration, the pattern of the connectors on the light source may align with the corners of the body of the dressing, as shown in FIG. 4B. In such embodiments, the dressing 2 and light source 12 may be restricted to one or two orientations of 180 degrees rotation relative to each other if the dressing is a rectangle. Alternatively, if the dressing is a square, the magnets may enable four orientations of 90 degrees of rotation relative to each other. In some embodiments, the connectors may be square, rectangle, circle, oval, diamond, hexagon, triangle, or any other shape. Alternatively or additionally, the connector may include a first dimension longer than a second dimension to force alignment between the dressing and the light source, for example if the connector 14 is positioned in the middle of the body of the dressing 2 or light source, as shown in the embodiment of FIG. 4C.

Figure 5:
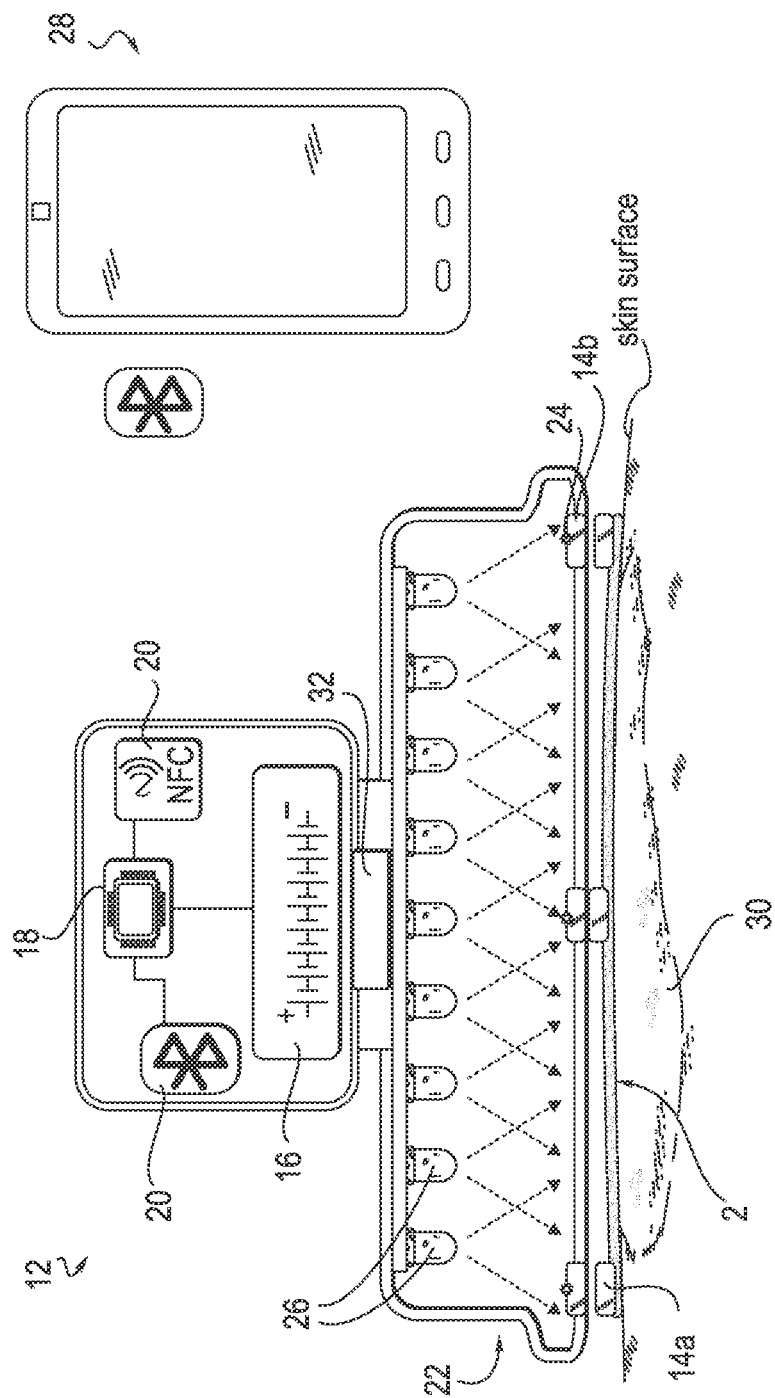
FIG. 5 illustrates one embodiment of a system with a shutdown circuit.

FIG. 5 illustrates one embodiment of a system with a safety (e.g., shutdown circuit 32). The shutdown circuit 32 may function to disengage the dressing 2 from the light source 12 or turn off the light source during adverse or harmful events. For example, the shutdown circuit 32 may turn off some of or all the lights of the light source to prevent overheating or heating beyond a certain amount determined by the physical limits of proper function of the light source or to prevent damage to the skin of the patient. In some embodiments, the shutdown circuit 32 may directly measure the light source temperature with a thermistor or with a control circuit that is preprogrammed to limit the use time of one or more of the LEDs. Further, temperature limitations on the circuit may ensure that the LEDs maintain their specified wavelengths. Further, in some embodiments, the dressing may include a color changing temperature sensitive strip to indicate a temperature of the dressing.

Figure 7:
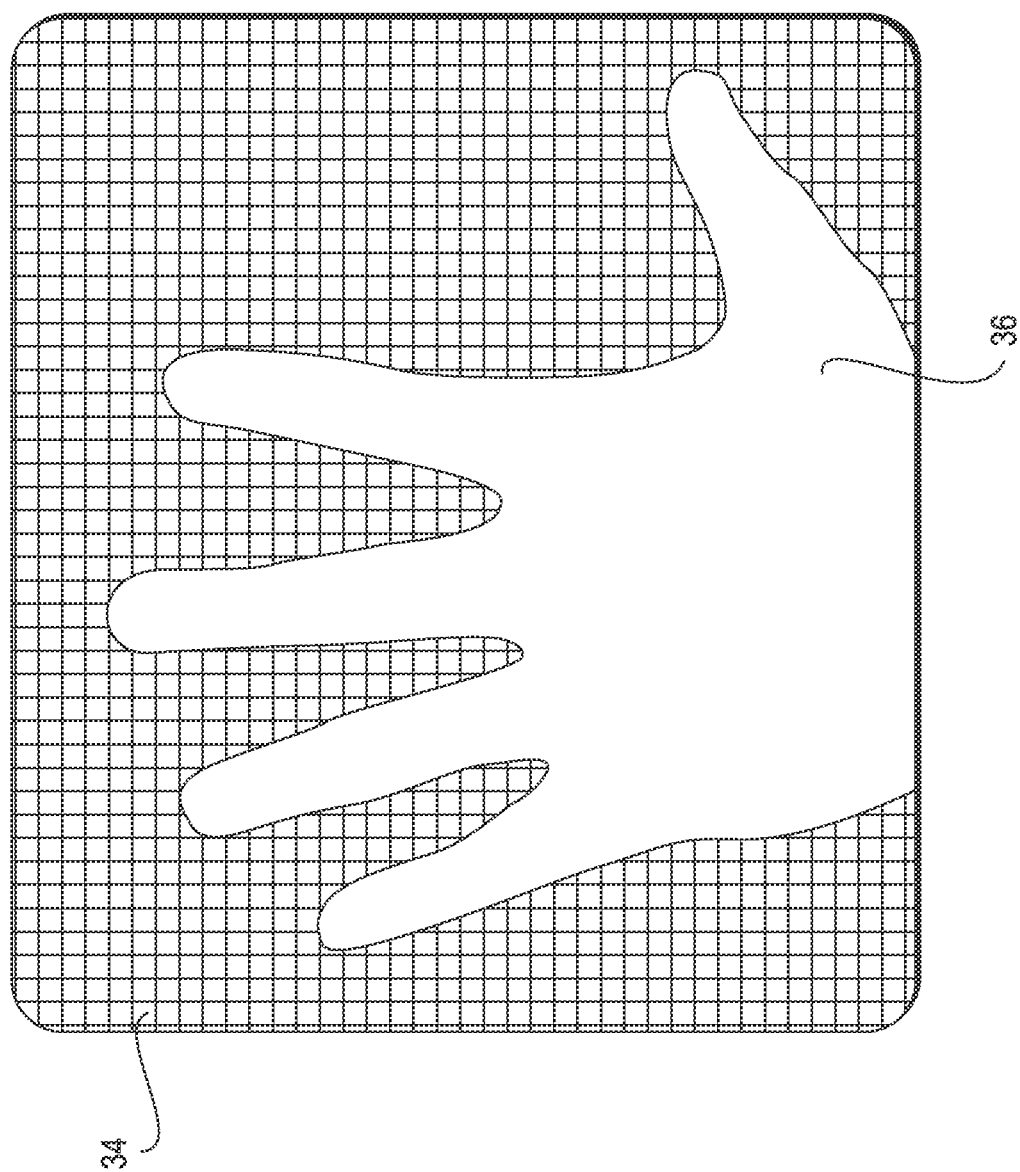
FIG. 7 illustrates a location indexing system for a person's hand(s) and/or feet.

FIG. 7 illustrates a location indexing system 34 for a person's hand(s) and/or foot/feet 36. A location indexing system functions to provide location indexing of the tips of the fingers or toes for easy repeated dosing of light to a lesion on the hands or feet. This system could be useful in directing light to the same spot on the hands or feet each day without having to wear gloves or small dressings around the small dimensions of the toes and fingers. Further, a location indexing system may be form fitting like a glove or be indexed by the tips of the feet and toes, such that the extremity is fully inserted to allow proper directing of light. The locating system may be made of a material that is transparent to ultraviolet light and fits various sizes of hands/feet. The indexing system may be a grid pattern on a flat surface to easily locate the light on a specific hand/foot location, as shown in FIG. 7. It may have connectors that allow for easy attachment of a light source. The connectors could be magnetic or ferromagnetic for example.

In some embodiments, a system for treating skin disorders by UV phototherapy may include a telehealth light therapy system. The telehealth light therapy system may function to optimize the amount of light delivered to a lesion and minimize the amount of light delivered to healthy skin. In one embodiment, a telehealth system may include one or more digital cameras; software for edge detection of lesion and identifying induration, redness and scale of a lesion; software configured to adjust the treatment dose and light beam size and shape based on lesion edge, lesion characteristics (e.g., induration, redness and scale), previous dose history, skin type, and/or patient feedback on skin sensitivity; a UV light source capable of changing the size and shape of the light beam; and contact sensor for ensuring a specific distance between a patient's skin and the light source. In some embodiments, the telehealth system may be installed into a stand-alone teleheath unit and be connected to a computer via a USB connection. Alternatively, the telehealth system may be connected to the light source, a mobile device in communication with the light source, or any other computing device. In some embodiments, the telehealth system may be configured to calculate a lesion's healing progress based on redness, scale, and induration. In some embodiments, a remote doctor may monitor the progress of the patient's lesions after treatment using the telehealth system.

Methods

Any of the apparatuses described herein may be used to treat a patient for a disorder, such as a skin disorder. For example, the dressings and/or phototherapy UV light sources described herein may be used to treat a patient for a skin disorders such as psoriasis.

In general, a method of treating a patient may include applying a medicament to the patient (e.g., applying the hydrogel and agent such as coal tar, as described above, so that the medicament occludes less than a target percentage, e.g., 50%, of UV light in the therapeutic wavelength range, e.g., 300-320 nm), and then applying UV light. For example, the medicament may be applied using a dressing, e.g., the medicament may be incorporated into the dressing, and UV light may be applied through the medicament (and any intervening region of the dressing) at a desired dose (e.g., light intensity and duration). Multiple locations may be treated sequentially or simultaneously on the patient's body. The dosage and/or treating regimen (e.g., number and timing of therapeutic doses) may be determined before or during treatment. Multiple doses may be applied during the same day. In general, dosing with UV may be concurrent with the delivery of therapeutic agent (e.g., coal tar and/or coal tar extract) from the dressing.

Figure 8:
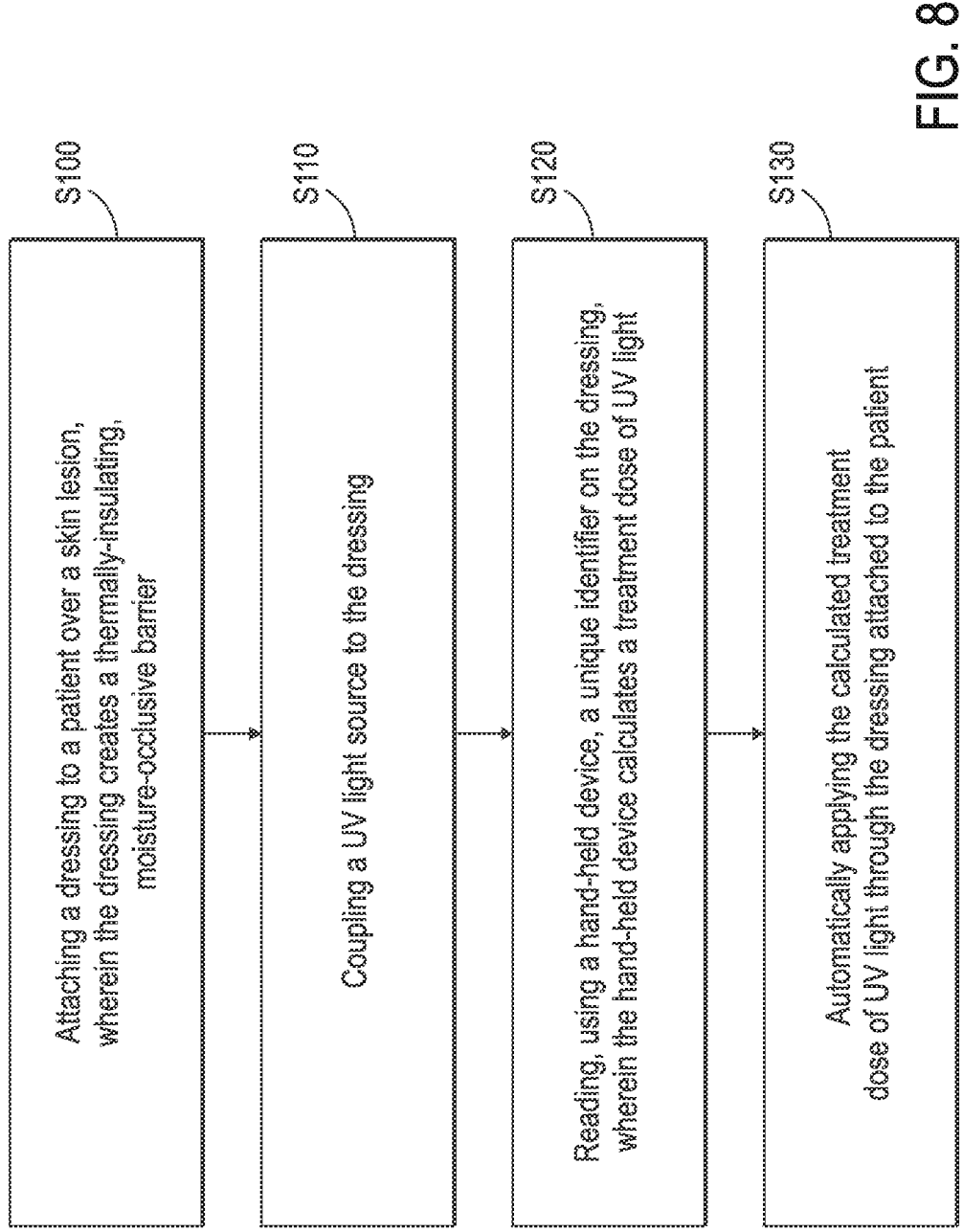
FIG. 8 illustrates a method for treating psoriasis by UV phototherapy.

FIG. 8 illustrates one example of a method for treating psoriasis by UV phototherapy. In this embodiment, the method includes attaching a dressing to a patient over a skin lesion, such that the dressing creates a thermally-insulating, moisture-occlusive barrier, and the dressing used is configured to occludes less than a target percent (e.g., 50%) of UV light at wavelengths in a therapeutic range (e.g., between 300 and 320 nm) S100. The UV light source may be coupled to the dressing S110. The UV light source may be configured as described above, to provide UV light at a dose (light intensity and duration), and may include any of the features described above, including interlock/confirmation of contact with the patient and/or dressing, etc. For example, the UV light source may communicate with the dressing and/or with a remote processor such as a smartphone or other device operating control logic. Thus, in some variations a handheld device may read an identifier on the dressing. The handheld device may confirm the timing of the dose (e.g., indicating, to a user, to attach the UV light source to the dressing/patient) and/or may calculate a treatment dose of UV light S120. The handheld device may then automatically apply the calculated treatment dose of UV light through the dressing attached to the patient S130. In some variations a separate handheld device is not necessary, and the dosage may be manually selected for the UV light source. Alternatively the UV light source may assume the functions of the handheld device described herein, such as calculating the dose and/or reading an identifier on the dressing.

Thus, described herein are methods to treat a skin lesion (e.g., psoriasis) on a patient using a dressing coupled to a therapeutic light source, for example a UV light source. Alternatively, the methods may be used in any wound healing or light therapy application, clinical or otherwise.

As shown in FIG. 8, one embodiment of a method for treating psoriasis by UV phototherapy includes attaching a dressing to a patient over a skin lesion, such that the dressing creates a thermally-insulating, moisture-occlusive barrier, and the dressing occludes less than 50% of UV light at wavelengths between 300 and 320 nm S100. In some variations the method includes a two step process including applying a medicament, for example a viscous coal tar gel, or the hydrogel with coal tar, to a skin region and then positioning a dressing over the medicament. Any of the dressings described herein do not need to be thermally-insulating or moisture-occlusive, but these optional features may be beneficial. In some embodiments, the dressing occludes little to no UV light, such that substantially all UV light may pass through the dressing. The dressing may be sized and configured to cover only the skin lesion, such that adjacent skin areas not requiring light therapy are excluded from the area covered by the dressing. In some embodiments, two or more dressings may be positioned adjacent to one another to achieve a larger treatment area.

A method for treating psoriasis by UV phototherapy may include coupling a UV light source to the dressing S110, which may be performed before, after or during calculation of the dose. The UV light source may be aligned and coupled with the dressing to permit UV light treatment of a skin lesion while reducing or preventing UV light treatment of healthy skin adjacent to the skin lesion. Coupling and alignment may be performed as described above. For example, in one embodiment, a first connector on the dressing, for example a magnet, aligns and couples the dressing with a light source including a second connector, for example a magnet.

As shown in FIG. 8, a method for treating psoriasis by UV phototherapy may include reading (e.g., using a handheld device) a unique identifier on the dressing, wherein upon reading the unique identifier, the handheld device calculates a treatment dose of UV light S100. In some embodiments, a handheld device is a light source (e.g., UV light source), a mobile device, a scanner, or any other computing device. In one embodiment, the handheld device includes a UV light source. In some embodiments, the handheld device may use one or more parameters to calculate the treatment dose of UV light. For example, the calculation may be based on a type of disease, a skin type, a patient feedback on a sensitivity of a lesion or group of lesions, a previous dose history, an amount of UV light absorbed by the dressing, an edge detection for recognition and guidance of the UV light, an amount of induration, an amount of scale, an amount of redness, a location of the lesion, an amount of UV light absorbed by the dressing, and/or the thickness of the epidermis. The calculation may include algorithms based on published guidelines for therapeutic light treatment of specific conditions like psoriasis, for example the American Academy of Dermatology's algorithm for narrowband ultraviolet B light from "Guidelines of care for the management of psoriasis and psoriatic arthritis, Section 5. Guidelines of care for the treatment of psoriasis with phototherapy and photochemotherapy."

As shown in FIG. 8, a method of treating psoriasis by UV phototherapy may include automatically applying the calculated treatment dose of UV light through the dressing attached to the patient S130. In some embodiments, the light source may detect a coupling between the light source and the dressing, and in some embodiments, the light source may automatically apply the UV phototherapy only once the connection is detected. Alternatively, a user may be prompted to initiate a phototherapy session once the light source detects a connection to the dressing. In some embodiments, a user may override or adjust the calculated treatment dose based on one or more parameters, for example a prescription from a physician.

The systems and methods of the preferred embodiment and variations thereof can be embodied and/or implemented at least in part as or by a machine configured to receive a computer-readable medium storing computer-readable instructions. The instructions are preferably executed by computer-executable components preferably integrated with the system and one or more portions of the processor and/or the controller. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all subranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A phototherapy dressing for treating psoriasis, the dressing comprising:
   a support body having an island region;
   a medicament in communication with the island region, the medicament comprising a hydrogel including a suspension of between 0.1% and 5% (by weight/volume) coal tar or coal tar extract mixed in the hydrogel, wherein the hydrogel comprises greater than 90% water and is between 0.005 to 0.1 inches thick;
   wherein the medicament and island region together occlude less than 50% of UV light at wavelengths between 300 and 320 nm from passing through the phototherapy dressing; and
   a magnetic attachment for a phototherapy UV light source on the support body, the magnetic attachment configured to secure the phototherapy UV light source over the island region of the phototherapy dressing.

2. The phototherapy dressing of claim 1, further comprising an adhesive on the phototherapy dressing peripheral to the island region.

3. The phototherapy dressing of claim 1, wherein the phototherapy dressing has a moisture vapor transmission of less than 2.3 g/m$^2$/h.

4. The phototherapy dressing of claim 1, wherein the support body comprises polyurethane.

5. The phototherapy dressing of claim 1, wherein the support body comprises a thin layer of polymeric material having a thickness of less than 0.005 inches.

6. The phototherapy dressing of claim 1, wherein the hydrogel is between 0.01 inches to 0.08 inches thick.

7. The phototherapy dressing of claim 1, wherein the phototherapy dressing has a thickness of less than 0.5 cm.

8. The phototherapy dressing of claim 1, wherein the medicament is layered onto the support body.

9. The phototherapy dressing of claim 1, wherein the island region comprises a roughened surface region on the support body.

10. The phototherapy dressing of claim 1, wherein the phototherapy dressing has a thermal conductivity of less than 0.32 W/m/° C.

11. The phototherapy dressing of claim 1, further comprising a unique identifier associated with the phototherapy dressing.

12. The phototherapy dressing of claim 1, further comprising a unique identifier associated with the phototherapy dressing, wherein the unique identifier is one of: an RFID tag, an optical code, a magnetic signature, or an alphanumeric code.

13. The phototherapy dressing of claim 1, wherein the hydrogel comprises greater than 95% water.

14. The phototherapy dressing of claim 1, wherein the magnetic attachment comprises a plurality of magnets on the support body.

15. A phototherapy dressing for treating psoriasis, the dressing comprising:
a support body;
a medicament in communication with the support body, the medicament comprising a hydrogel including a suspension of between 0.1% and 5% (by weight/volume) coal tar or coal tar extract mixed in the hydrogel, wherein the hydrogel comprises greater than 90% water and is between 0.005 to 0.1 inches thick;
wherein the medicament and support body together occlude less than 50% of UV light at wavelengths between 300 and 320 nm from passing through the phototherapy dressing;
an adhesive on the phototherapy dressing; and
a magnetic attachment for a phototherapy UV light source on the support body, the magnetic attachment configured to secure the phototherapy UV light source to the phototherapy dressing.

16. The phototherapy dressing of claim 15, wherein the support body forms an island region in which the medicament is positioned, and the adhesive is located peripheral to the island region on the phototherapy dressing.

17. The phototherapy dressing of claim 15, wherein the phototherapy dressing has a moisture vapor transmission of less than 2.3 g/m²/h.

18. The phototherapy dressing of claim 15, wherein the support body comprises polyurethane.

19. The phototherapy dressing of claim 15, wherein the support body comprises a thin layer of polymeric material having a thickness of less than 0.005 inches.

20. The phototherapy dressing of claim 15, wherein the phototherapy dressing has a thickness of less than 0.5 cm.

21. The phototherapy dressing of claim 15, wherein the hydrogel is between 0.01 inches to 0.08 inches thick.

22. The phototherapy dressing of claim 15, wherein the medicament is layered onto the support body.

23. The phototherapy dressing of claim 15, wherein the medicament is positioned within an island region comprising a roughened surface region on the support body.

24. The phototherapy dressing of claim 15, wherein the phototherapy dressing has a thermal conductivity of less than 0.32 W/m/° C.

25. The phototherapy dressing of claim 15, further comprising a unique identifier associated with the phototherapy dressing.

26. The phototherapy dressing of claim 15, further comprising a unique identifier associated with the phototherapy dressing, wherein the unique identifier is one of: an RFID tag, an optical code, a magnetic signature, or an alphanumeric code.

27. The phototherapy dressing of claim 15, wherein the hydrogel comprises greater than 95% water.

28. The phototherapy dressing of claim 15, wherein the magnetic attachment comprises a plurality of magnets on the support body.

29. A phototherapy dressing for treating psoriasis, the dressing comprising:
a support body;
a medicament in communication with the support body, the medicament comprising a hydrogel including a suspension of between 0.1% and 5% (by weight/volume) coal tar or car tar extract mixed in the hydrogel, wherein the hydrogel comprises greater than 90% water and is between 0.005 to 0.1 inches thick;
wherein the medicament and support body together occlude less than 50% of UV light at wavelengths between 300 and 320 nm from passing through the phototherapy dressing;
an adhesive on the phototherapy dressing;
a unique identifier on the support body associated with the phototherapy dressing; and
a magnetic attachment for a phototherapy UV light source on the support body, the magnetic attachment configured to secure the phototherapy UV light source to the phototherapy dressing.

* * * * *